US009982062B2

(12) United States Patent
Harriman

(10) Patent No.: US 9,982,062 B2
(45) Date of Patent: *May 29, 2018

(54) IN VIVO METHOD FOR GENERATING DIVERSITY IN A PROTEIN SCAFFOLD

(71) Applicant: Crystal Bioscience Inc., San Diego, CA (US)

(72) Inventor: William Don Harriman, Alameda, CA (US)

(73) Assignee: CRYSTAL BIOSCIENCE INC., San Diego, CA (US)

( * ) Notice: Subject to any disclaimer, the term of this patent is extended or adjusted under 35 U.S.C. 154(b) by 69 days.

This patent is subject to a terminal disclaimer.

(21) Appl. No.: 15/177,280

(22) Filed: Jun. 8, 2016

(65) Prior Publication Data
US 2016/0304626 A1  Oct. 20, 2016

Related U.S. Application Data

(63) Continuation of application No. 14/241,806, filed as application No. PCT/US2012/060365 on Oct. 16, 2012, now Pat. No. 9,394,372.

(60) Provisional application No. 61/550,261, filed on Oct. 21, 2011.

(51) Int. Cl.
A01N 63/00     (2006.01)
C07K 16/46     (2006.01)
A01K 67/027    (2006.01)
C07K 16/00     (2006.01)

(52) U.S. Cl.
CPC ........ C07K 16/462 (2013.01); A01K 67/0275 (2013.01); A01K 67/0278 (2013.01); C07K 16/005 (2013.01); C07K 16/468 (2013.01); A01K 2207/15 (2013.01); A01K 2217/05 (2013.01); A01K 2217/052 (2013.01); A01K 2227/101 (2013.01); A01K 2227/102 (2013.01); A01K 2227/103 (2013.01); A01K 2227/107 (2013.01); A01K 2227/30 (2013.01); A01K 2267/01 (2013.01); C07K 2317/14 (2013.01); C07K 2317/23 (2013.01); C07K 2317/24 (2013.01); C07K 2317/31 (2013.01); C07K 2317/52 (2013.01); C07K 2317/56 (2013.01); C07K 2317/569 (2013.01); C07K 2317/622 (2013.01); C07K 2317/64 (2013.01)

(58) Field of Classification Search
None
See application file for complete search history.

(56) References Cited

U.S. PATENT DOCUMENTS 8,592,644 B2    11/2013 Harriman et al.
9,394,372 B2 *   7/2016 Harriman ............ C07K 16/005
2002/0042366 A1   4/2002 Thompson et al.
2002/0108132 A1   8/2002 Rapp
2006/0034845 A1   2/2006 Silence et al.
2010/0138946 A1   6/2010 Van de Lavoir et al.
2011/0055938 A1   3/2011 Harriman et al.

FOREIGN PATENT DOCUMENTS

WO    WO2011018421    2/2011

OTHER PUBLICATIONS

Etches et al. Strategies for the production of transgenic chickens. In Methods in Mole Biol 1997, vol. 62, pp. 433-450. Tuan Edits.*
Houdebine, 1994 J. Biotech. 34, p. 269-87.*
Mullins J Clin Invest, 1996;97:1557-60.*
Wall, J Dairy Sci 1997;80:2213-24.*
Nishijima et al. Develop Growth Differ 2013;55:207-16.*
Dyck, et al. "Making recombinant proteins in animals—different systems, different applications", Trends in Biotechnology, 2003, 21(9) 394-399.
Gebauer, et al. "Engineered protein scaffolds as next-generation antibody therapeutics", Current Opinion in Chemical Biology, 2009, 13: 245-255.
Harris, et al. "AID Is Essential for Immunoglobulin V Gene Conversion in a Cultured B Cell Line", Current Biology, vol. 12, 435-438, Mar. 5, 2002.
Kanayama, et al. "Genetic manipulation of an exogenous non-immunoglobulin protein by gene conversion machinery in a chicken B cell line", Nucleic Acids Research, 2006, vol. 34, No. 2.
Kim, et al. "Migration and Proliferation of Intact and Genetically Modified Primordial Germ Cells and the Generation of a Transgenic Chicken", Biology of Reproduction, 2010, 82: 257-262.
Leighton, et al. "A diverse repertoire of human immunoglobulin variable genes in a chicken B cell line is generated by both gene conversion and somatic hypermutation", Frontiers in Immunology, B Cell Biology, Mar. 2015, vol. 6, Article 126, pp. 1-8.
Lillico, et al. "Transgenic chickens as bioreactors for protein-based drugs", DDT, 2005, 10: 191-196.
McCormack, et al. "Germ Line Maintenance of the Pseudogene Donor Pool for Somatic Immunoglobulin Gene Conversion in Chickens", Molecular and Cellular Biology, 1993, 13(2): 821-830.
Ratcliffe, "Antibodies, immunoglobulin genes and the bursa of Fabricius in chicken B cell development", Development and Comparative Immunology, 2006, 30: 101-118.
Shusser, et al. "Harnessing Gene Conversion in Chicken B Cells to Create a Human Antibody Sequence Repertoire", PLOS One, Nov. 2013, vol. 8, Issue 11, e80108, pp. 1-15.

(Continued)

Primary Examiner — Janice Li
(74) Attorney, Agent, or Firm — James S. Keddie; Bozicevic, Field & Francis, LLP

(57) ABSTRACT

A transgenic non-human animal is provided. In certain embodiments, the animal comprises a genome comprising an immunoglobulin heavy chain locus comprising: a) a transcribed gene encoding a fusion protein comprising, from N-terminus to C-terminus: i. a scaffold comprising a first binding domain; and ii. a heavy chain constant region operably linked to the scaffold; wherein the scaffold is capable of specifically binding to a target in the absence of additional polypeptides; and b) a plurality of pseudogenes that are operably linked to the transcribed gene and that donate, by gene conversion, nucleotide sequence to the part of the transcribed gene that encodes the binding domain.

15 Claims, 5 Drawing Sheets

(56) References Cited

OTHER PUBLICATIONS

Song, et al. "Characteristics of Long-Term Cultures of Avian Primordial Germ Cells and Gonocytes1", Biology of Reproduction (2014) 90(1):15, 1-8.
Van De Lavoir, et al. "Germline transmission of genetically modified primordial germ cells", Nature, vol. 441, Jun. 8, 2006, pp. 766-769.
Yang, et al. "Control of gene conversion and somatic hypermutation by immunoglobulin promoter and enhancer sequences", JEM, vol. 203, No. 13, Dec. 25, 2006, 2919-2928.
Ching et al., "Chickens with humanized immunoglobulin genes generate antibodies with high affinity and broad epitope coverage to conserved targets", MABS, 2017, 0(0):1-10.

* cited by examiner

IN VIVO METHOD FOR GENERATING DIVERSITY IN A PROTEIN SCAFFOLD

BACKGROUND

Many types of proteins have the capacity to serve as a scaffold for the creation of new binding proteins that can be used as a therapeutic or diagnostic. Such scaffolds generally contain a relatively invariant "framework" region that provides structure to the scaffold, and other more substitution-tolerant regions that make contact with and provide for specific binding to a target. The amino acid sequence of the contact regions are typically different for each target. The contact regions may be solvent exposed, and can be adjacent to each other or on opposite sides of the scaffold protein, depending on the nature of the scaffold. Due to the wide range of structures, there is considerable opportunity to develop custom molecules with commercial application. Indeed, there are engineered scaffolds currently in clinical development.

Current scaffold methodologies generally lack an in vivo process by which both genetic diversification and clonal selection can occur.

SUMMARY

A transgenic non-human animal is provided. In certain embodiments, the animal comprises a genome comprising an immunoglobulin heavy chain locus comprising: a) a transcribed gene encoding a fusion protein comprising, from N-terminus to C-terminus: i. a scaffold comprising a first binding domain; and ii. a heavy chain constant region operably linked to the scaffold; wherein the scaffold is capable of specifically binding to a target in the absence of additional polypeptides; and b) a plurality of pseudogenes that are operably linked to the transcribed gene and that donate, by gene conversion, nucleotide sequence to the part of the transcribed gene that encodes the binding domain.

In some embodiments, the animal may additionally comprise an immunoglobulin light chain locus that encodes a light chain constant region but not a light chain variable domain, where the fusion protein encoded by the heavy chain locus and the light chain constant region encoded by the light chain locus, when expressed, link together via a disulfide bond in the same was a classical antibody.

In other embodiments, the animal may additionally comprise an immunoglobulin light chain locus comprising: a) a second transcribed gene encoding a second fusion protein comprising, from N-terminus to C-terminus: i. a second scaffold comprising a second binding domain; and ii. a light chain constant region operably linked to the scaffold; wherein the scaffold is capable of specifically binding to a target in the absence of additional polypeptides; and b) a plurality of pseudogenes that are operably linked to the second transcribed gene and that donate, by gene conversion, nucleotide sequence to the part of the second transcribed gene that encodes the second binding domain. In these embodiments, the first and second binding domains may have different binding specificities.

Method for making fusion proteins that employ the subject animal, as well as fusion proteins made by the same are also provided.

DEFINITIONS

Figure 1:
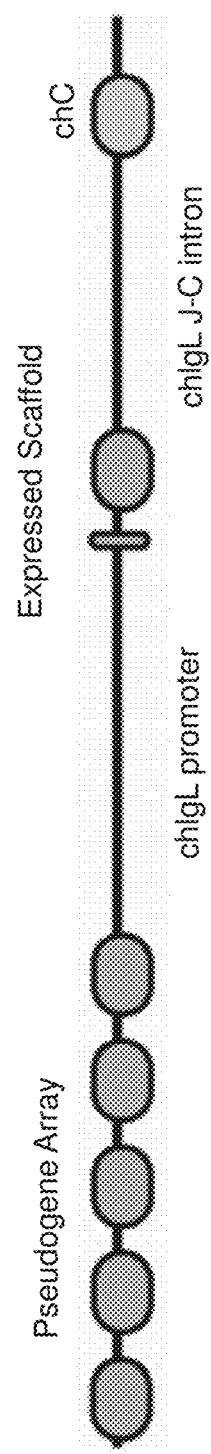
FIG. 1 schematically illustrates an example of a subject immunoglobulin heavy chain locus.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "gene" refers to a nucleic acid sequence comprised of a promoter region, a coding sequence, and a 3'UTR.

The terms "protein" and "polypeptide" are used interchangeably herein.

A "leader sequence" is a sequence of amino acids present at the N-terminal portion of a protein which facilitates the secretion of the mature form of the protein from the cell. The definition of a signal sequence is a functional one. The mature form of the extracellular protein lacks the signal sequence, which is cleaved off during the secretion process.

The term "nucleic acid" encompasses DNA, RNA, single stranded or double stranded and chemical modifications thereof. The terms "nucleic acid" and "polynucleotide" are used interchangeably herein.

A "non-human" animal refers to any animal of a species that is not human.

The term "progeny" or "off-spring" refers to any and all future generations derived and descending from a particular animal. Thus, progeny of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal. Alternatively, a transgenic animal may be produced by transfer of a nucleus from a genetically modified somatic cell or by transfer of a genetically modified pluripotential cell such as an embryonic stem cell or a primordial germ cell.

The term "intron" refers to a sequence of DNA found in the middle of many gene sequences in most eukaryotes. These intron sequences are transcribed, but removed from within the pre-mRNA transcript before the mRNA is translated into a protein. This process of intron removal occurs by splicing together of the sequences (exons) on either side of the intron.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an intron is operably-linked to a coding sequence, the intron is spliced out of the mRNA to provide for expression of the coding sequence. In the context of gene conversion, two nucleic acids sequences are operably linked if one sequence can "donate" sequence to the other by gene conversion. If two sequences are unlinked in that one can donate sequence to the other via gene conversion, the donating sequences may be upstream or downstream of the other, and the two sequences may be proximal to each other, i.e., in that there are no other intervening genes. "Unlinked" means that the associated genetic elements are not closely associated with one another and the function of one does not affect the other.

The terms "upstream" and "downstream" are used with reference to the direction of transcription.

The term "pseudogene" is used to describe an untranscribed nucleic acid region that contains an open reading frame that may or may not contain a start and/or a stop codon. An amino acid sequence may be "encoded" by a pseudogene in the sense that the nucleotide sequence of the open reading frame can be translated in silico to produce an amino acid sequence. Pseudogenes do not contain promoter regions, recombination signal sequences or leader sequences.

A "transcribed gene" is a gene that is operably lined to a promoter and terminator, and has a coding sequence that is transcribed and translated into a protein product.

The term "homozygous" indicates that identical alleles reside at the same loci on homologous chromosomes. In contrast, "heterozygous" indicates that different alleles reside at the same loci on homologous chromosomes. A transgenic animal may be homozygous or heterozygous for a transgene.

The term "native", with reference to a gene or protein, indicates that the gene or protein is endogenous to a species, i.e., the gene is present at a particular locus in the genome of a non-modified organism of that species.

The term "construct" refers to a recombinant nucleic acid, generally recombinant DNA, that has been generated for the purpose of the expression of a specific nucleotide sequence(s), or is to be used in the construction of other recombinant nucleotide sequences. A construct might be present in a vector or in a genome.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide. If a cell receives a recombinant nucleic acid, the nucleic acid is "exogenous" to the cell.

The term "selectable marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "replacing", in the context of replacing one genetic locus with another, refers to a single step protocol or multiple step protocol.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA. Pseudogenes may contain an untranscribed coding sequence.

The term "in reverse orientation to" refers to coding sequences that are on different strands. For example, if a transcribed region is described as being in reverse orientation to a pseudogene, then the amino acid sequence encoded by the transcribed region is encoded by the top or bottom strand and the amino acid sequence encoded by the pseudogene is encoded by the other strand relative to the transcribed region.

It is understood that the binding proteins produced by the present method may have additional conservative amino acid substitutions which have substantially no effect on binding or other functions. By conservative substitutions is intended combinations such as those from the following groups: gly, ala; val, ile, leu; asp, glu; asn, gln; ser, thr; lys, arg; and phe, tyr. Amino acids that are not present in the same group are "substantially different" amino acids.

The term "specific binding" refers to the ability of a binding protein to preferentially bind to a particular target that is present in a homogeneous mixture of different analytes. In certain embodiments, a specific binding interaction will discriminate between desirable and undesirable target in a sample, in some embodiments more than about 10 to 100-fold or more (e.g., more than about 1000- or 10,000-fold).

In certain embodiments, the affinity between a binding protein and target when they are specifically bound in an binding protein/target complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

As used herein the term "isolated," when used in the context of an isolated protein, refers to protein that is at least 60% free, at least 75% free, at least 90% free, at least 95% free, at least 98% free, and even at least 99% free from other components with which the protein is associated with prior to purification.

The term "introduced" in the context of inserting a nucleic acid sequence into a cell, means "transfection", or "transformation", or "transduction" and includes reference to the incorporation of a nucleic acid sequence into a eukaryotic or prokaryotic cell wherein the nucleic acid sequence may be present in the cell transiently or may be incorporated into the genome of the cell (e.g., chromosome, plasmid, plastid, or mitochondrial DNA), converted into an autonomous replicon.

The term "plurality" refers to at least 2, at least 5, at least 10, at least 20, at least 50, at least 100, at least 200, at least 500, at least 1000, at least 2000, at least 5000, or at least 10,000 or at least 50,000 or more. In certain cases, a plurality includes at least 10 to 50. In other embodiments, a plurality may be at least 50 to 1,000.

The terms "antibody" and "immunoglobulin" are used interchangeably herein. These terms are well understood by those in the field, and refer to a protein consisting of one or more polypeptides that specifically binds an antigen. One form of an antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, and scFv fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, $F(ab')_2$, and or other antibody fragments that retain specific binding to antigen, and monoclonal antibodies.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

An immunoglobulin light or heavy chain variable region consists of a "framework" region (FR) interrupted by three hypervariable regions, also called "complementarity determining regions" or "CDRs". The extent of the framework region and CDRs have been precisely defined (see, Lefranc et al, IMGT, the international ImMunoGeneTics information system. Nucleic Acids Res. 2009 vol. 37 (Database issue): D1006-12. Epub 2008 Oct. 31; see worldwide website of imgt.org and referred to hereinafter as the "IMGT system")). The numbering of all antibody amino acid sequences discussed herein conforms to the IMGT system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a chicken or rabbit monoclonal antibody may be joined to human constant segments, such as gamma 1 and gamma 3. An example of a therapeutic chimeric antibody is a hybrid protein composed of the variable or antigen-binding domain from a chicken or rabbit antibody and the constant or effector domain from a human antibody (e.g., the anti-Tac chimeric antibody made by the cells of A.T.C.C. deposit Accession No. CRL 9688), although other mammalian species may be used.

As will be described in greater detail below, an antibody may be "classical antibody" or a "single chain antibody".

For the purposes of this disclosure, a "classical antibody" is a stereotypical "Y"-shaped molecule that consists of four polypeptide chains; two identical heavy chains and two identical light chains connected by disulfide bonds. Each chain is composed of an N-terminal variable domain ($V_H$ for the heavy chain and $V_L$ for the light chain) that is approximately 110 amino acids long and a C-terminal constant domain ($C_H$ for the heavy chain and $C_L$ for the light chain) that varies in type and length, depending on the type of antibody. The heavy and light chains of a classical antibody are held together by interactions between conserved cysteines (which occur in the heavy and light constant domains) and other charged amino acids. Sequence variability in a classical antibody is concentrated in the antigen binding site of the antibody, which are at the type of the arms of the Y. These regions are defined by the "complementarity-determining regions" ("CDRs") that are interspersed with regions that are more conserved, termed "framework regions". Each of the heavy and light chain variable domains contains three CDRs (called CDR1, CDR2 and CDR3). In a classical antibody, all six CDRs and both heavy and light variable domains are required for antigen binding. Classical antibodies are made by human, mice, rabbits, chicken and cattle, for example.

For the purposes of this disclosure, a "single chain antibody" is an antibody that contains an antigen binding site that is composed of a single polypeptide chain. One example of a single chain antibody is a single-chain variable fragment (scFv) antibody, which is a fusion protein that contains the variable regions of the heavy (VH) and light chains (VL) of a classical antibody connected by a short linker peptide of ten to about 25 amino acids. A single-chain antibody can also be obtained by immunization of a camelid (e.g., a camel, llama or alpaca) or a cartilaginous fish (e.g., a shark), which make antibodies that are composed of only heavy chains. A monomeric variable domain of a heavy chain antibody binds antigen. The nucleotide sequence of a single chain antibody may be derived from a germline sequence or an mRNA sequence, for example. A classical antibody is not a single chain antibody because both the heavy and light chains are required for antigen binding in a classical antibody.

A "natural" antibody is an antibody in which the heavy and light immunoglobulins of the antibody have been naturally selected by the immune system of a multi-cellular organism. Spleen, lymph nodes and bone marrow are examples of tissues that produce natural antibodies in an animal.

As used herein, the term "scaffold" refers to any monomeric protein (i.e., a protein that is composed of a single chain of amino acids that is encoded by a single gene) that has a target binding domain and that can autonomously (i.e., without additional polypeptides) bind to a target. A scaffold contains a "framework", which is largely structural, and a "binding domain" which makes contact with the target and provides for specific binding. The binding domain of a scaffold need not be defined by one contiguous sequence of the scaffold. In certain cases, a scaffold may be part of larger binding protein, which, itself, may be part of a multimeric binding protein that contains multiple scaffolds. Certain multimeric binding proteins may be bi-specific in that they can bind to two different epitopes. "Biparatopic" binding proteins can bind two distinct epitopes on the same target.

A scaffold may be derived from (i.e., have the same structure as but not necessarily the same amino acid sequence as) a single chain antibody (as defined above), or a scaffold may be not antibody-derived, in which a case it may have no sequence or structural relation to an antibody variable domain. Classical antibodies require both a heavy chain and a light chain for binding and, as such, do not contain a scaffold that binds to a target in the absence of additional polypeptides.

As used herein, the term "immunoglobulin heavy chain locus" is a position of a genome that, in its wild-type form, encodes the heavy chain of an antibody.

As used herein, the term "immunoglobulin light chain locus" is a position of a genome that, in its wild-type form, encodes the light chain of an antibody.

As used herein, the term "heavy chain constant region" is the constant region of a heavy chain of an antibody.

As used herein, the term "not antibody derived" and grammatical equivalents thereof in the context of a scaffold refer to a scaffold that has neither the characteristic structure of a variable domain of an antibody, nor a sequence of at least 100 contiguous amino acids that is at least 80% identical to an amino acid sequence in the variable domain of an antibody. The term "not antibody derived" is intended to exclude single chain antibodies (i.e., the "only heavy chain" and scFv antibodies discussed above) as well as classical antibodies. Fibronectin type III domains (FN3's), Adnectins, DARPins, Affibodies, Avian Pancreatic Peptides (APPs), Lipocalins, Atrimers, Kringle Domains, Phylomers, Centyrins), etc. are examples of proteins that are not antibody derived. Other examples of scaffolds are described below.

As used herein, the term "gene conversion" refers to a well-known molecular phenomenon in which one allele of a sequence converts to another base mismatch repair during recombination.

As used herein, the term "a light chain constant region but not a light chain variable domain" and grammatical equivalents thereof refers to an antibody light chain that has been truncated to remove its variable domain while retaining the constant domain. The constant domain of a light chain that lacks a variable domain is full length and can dimerize with a heavy chain constant domain and produce a disulfide bond therewith.

Further definitions may be elsewhere in this disclosure.

DESCRIPTION OF EXEMPLARY EMBODIMENTS

Before the present subject invention is described further, it is to be understood that this invention is not limited to particular embodiments described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As noted above, a transgenic animal is provided. In certain embodiments, the animal may be any non-human animal that employs gene conversion for developing their primary antigen repertoire and, as such, the animal may be any of a variety of different animals. In one embodiment, the animal may be a bird, e.g., a member of the order Galliformes such as a chicken or turkey, or a member of the order Anseriformes such as a duck or goose, or a mammal, e.g., a lagamorph such as rabbit, or a farm animal such as a cow, sheep, pig or goat. In particular embodiments, the transgenic animal may be a non-rodent (e.g., non-mouse or non-rat), non-primate transgenic animal.

Some of this disclosure may describe a transgenic chicken having a heavy chain locus that contains a transcribed gene and pseudogenes. Since the nucleotide sequences of the immunoglobulin loci of many animals are known, as are methods for modifying the genome of such animals, the general concepts described below may be readily adapted to any suitable animal, i.e., any animal that employs gene conversion for developing their primary antigen repertoire. The generation of antibody diversity by gene conversion between the variable region of a transcribed immunoglobulin heavy or light chain gene and operably linked (upstream) pseudo-genes that contain different variable regions is described in a variety of publications such as, for example, Butler (Rev. Sci. Tech. 1998 17: 43-70), Bucchini (Nature 1987 326: 409-11), Knight (Adv. Immunol. 1994 56: 179-218), Langman (Res. Immunol. 1993 144: 422-46), Masteller (Int. Rev. Immunol. 1997 15: 185-206), Reynaud (Cell 1989 59: 171-83) and Ratcliffe (Dev. Comp. Immunol. 2006 30: 101-118).

As noted above, the genome of the subject transgenic animal may comprise a transcribed gene encoding a binding protein comprising, from N-terminus to C-terminus: i. a scaffold comprising a first binding domain; and ii. a heavy chain constant region operably linked to the scaffold. The scaffold is characterized in that, unlike a classical antibody, it is capable of specifically binding to a target autonomously, i.e., in the absence of additional polypeptides. The scaffold is not from a classical antibody. In certain embodiments, the scaffold may be the variable domain of a single chain antibody, or, in alternative embodiments, the scaffold is antibody-derived. Operably linked to the transcribed gene is a plurality of untranscribed pseudogenes that donate, by gene conversion, nucleotide sequence to the part of said transcribed gene that encodes the binding domain. In particular embodiments, the sequences may be arranged to parallel the endogenous heavy chain locus (shown in FIG. 1). As shown in FIG. 1, the sequences may be arranged in the same was as the endogenous heavy chain locus in the animal, e.g., from 5' to 3', as follows: a) the plurality of pseudogenes, b) a heavy chain promoter, c) an expressed scaffold that is transcribed by the heavy chain promoter, d) an intron, and e) a native heavy chain constant region, although other arrangements are possible.

In the transgenic animal, gene conversion between the binding domain-encoding part of the transcribed gene and the pseudogenes alters the sequence of the scaffold by gene conversion, by as little as a single nucleotide to multiple nucleotides distributed throughout the entire length of the binding domain, e.g., the entire length of the scaffold. Because: a) the arrangement of the sequences described herein mimics the wild-type immunoglobulin heavy chain locus and b) the fusion protein contains an endogenous constant domain, the scaffold is expected to undergo selection and affinity maturation in a similar way to antibodies in an unmodified host animal. In other words, in a subject animal, the scaffold may be diversified in vivo through the gene conversion mechanism that is native to the animal, and upon immunologic challenge, reactive lymphocytes may be selected via the animal's natural cellular selection process. Since the C region is native to the animal sequence, a functional antigen receptor is formed in the milieu of other proteins, and B lymphocyte development is normal. In certain cases, the animal may be thought of as one in which the active V region and pseudo-V array of the heavy chain locus of the animal are replaced with alternative scaffold sequences, thereby allowing the animal to optimize the interaction between the target and the binding domain of the alternative scaffold using the immune system of the animal. The fusion protein produced by the transgenic animal is therefore encoded by whatever sequence is donated from the pseudogenes into the transcribed gene. Clonal selection creates new sequences that are not encoded by the germline and are unique to each clonal population of B lymphocytes present within a single individual. Upon immunization, reactive clones can be selected and enriched on the basis of their antigen receptor, which is a cell surface fusion protein encoded by the transcribed gene. After selection, sequences encoding an optimized scaffold can be isolated using conventional methods (e.g., using hybridoma technology or by PCR, etc).

The scaffold encoded by the subject gene may be a single chain antibody (as defined above). In other embodiments, the scaffold that is not antibody derived. Examples of scaffolds that are not antibody derived include any non-antibody protein that is known to specifically bind to a target, particularly a protein target. Suitable scaffolds are described in Binz et al (*Engineered proteins as specific binding reagents*. Curr Opin Biotechnol. 2005 16:459-69), Binz et al (*Engineering novel binding proteins from nonimmunoglobulin domains*. Nat. Biotechnol. 2005 23:1257-68), Forrer et al (*Consensus design of repeat proteins*. Chembiochem. 2004 5:183-9), Grönwall et al (*Engineered affinity proteins—generation and applications*. J. Biotechnol. 2009 140:254-69), Hosse et al (*A new generation of protein display scaffolds for molecular recognition*. Protein Sci. 2006 15:14-27) and et al Skerra et al (*Alternative non-antibody scaffolds for molecular recognition*. Curr. Opin. Biotechnol. 2007 18:295-304), which are incorporated by reference for disclosure of specific types of scaffolds, examples of wild type proteins that are of a specific scaffold type and a description of the binding domain of such scaffolds. Further details of the listed scaffolds, the positioning of the binding domain and which proteins contain such binding domains, can be found in NCBI's conserved domain database and NCBI's Genbank database, which database entries are incorporated by reference.

Scaffolds of particular interest include, but are not limited to: α-helical binding domains (e.g., those based on Z domain proteins such as that from staphylococcal protein A; immunity proteins such as the *E. coli* colicin E7 and Im9 immunity proteins; Cytochrome b562 peptide; α2p8 and repeat proteins such as ankyrin repeat proteins and leucine-rich repeat proteins), scaffolds with irregular secondary structures (e.g., those based on insect defensin A; kunitz domain inhibitors such as BPTI, PSTI, APPI, LTDI, MTI II, ecotin, DX-88, LACI and HAE; PDZ domains such as AF-6 and Omi; charybdotoxin; scorpion toxins; insect defensins; PHD finger proteins such as CtBP2; TEM-1 and β-lactamase), and scaffolds with β-sheet structures (e.g., those based on the 10th fibronectin type III domain (FNR); CTLA-4; T-cell receptors; knottins such as EETI-II, CBD, and Min-23; neocarzinostatin; carbohydrate binding module 4-2; tendamistat; lipocalins; and green fluorescent protein) as described in Hosse, supra. Many other examples of suitable scaffolds are described in the literature. The initial scaffold of the transcribed does not need to bind to a known target because gene conversion will modify the sequence of the transcribed gene to produce a fusion protein that binds to the target. In particular cases, however, the initial scaffold may already bind to a known target. In these embodiments, the animal may in certain cases be employed to optimize binding to a target.

The number of pseudogenes upstream of the transcribed gene may vary greatly and in some embodiment may be in the range of 5 to 50, e.g., 10 to 30 in number. The pseudogenes may be different to one another in sequence, and may contain a number of point mutations that are distributed throughout the pseudogene array. The pseudogenes generally contain a nucleotide sequence that is at least 80% identical (e.g., at least 90%, identical at least 95% identical at least 98% identical) to at least the part of the transcribed gene that encodes the binding domain of the scaffold. In some embodiments, the pseudogenes may contain sequence that is related to only the binding domain encoding sequence of the scaffold. In other embodiments, the pseudogenes may contain sequence that is related to more than the binding domain encoding sequence of the scaffold, e.g., 15 bases either side, 50 bases either side, 100 bases either side or 200 bases either side, or more, up to entire length of scaffold encoding sequence. The spacing between the pseudogenes may vary. In certain embodiments, the spacing may be in the range of 50 to 1,000 bases.

In particular embodiments, at least one (e.g., at least 2, at least 3, at least 5, at least 10 or more) of the plurality of pseudogenes may be in reverse orientation relative to the transcribed gene. In particular embodiments, the plurality of pseudogenes are not in alternating orientations, and in certain cases may rather contain a series of at least 5 or at least 10 adjacent pseudogenes that are in opposite orientation relative to the transcribed gene. In one embodiment, the pseudogene that is most distal from the transcribed variable region is in the same orientation as the transcribed gene, and the pseudogene between the most distal pseudogene and the transcribed gene are in the reverse orientation relative to the transcribed gene.

Figure 2:
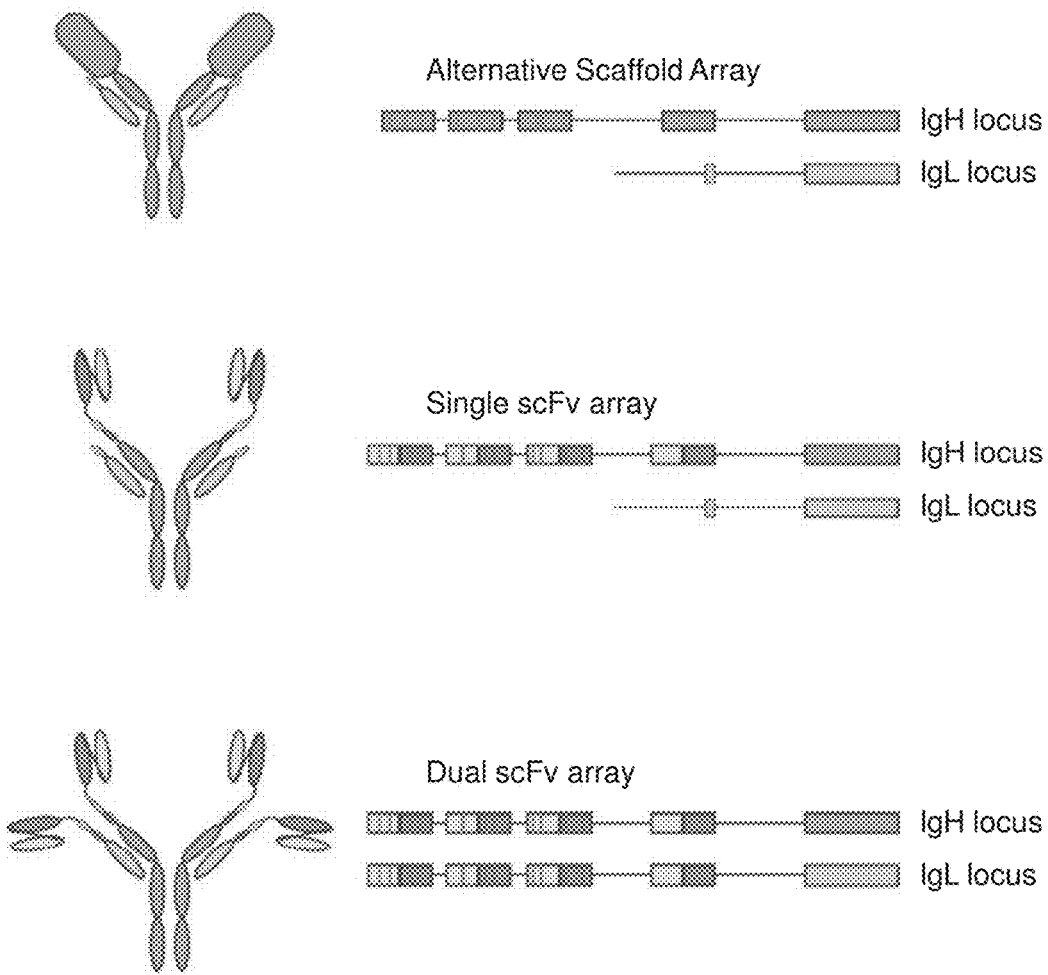
FIG. 2 schematically illustrates several types of binding proteins

In addition to having an immunoglobulin heavy chain locus discussed above, a transgenic animal in certain cases may also have a modified immunoglobulin light chain locus. In one embodiment the immunoglobulin light chain locus of the animal may be inactivated so that the animal produces no light chain constant domain and, as such, the animal produces only the fusion protein discussed above, i.e., without a light chain constant domain-containing protein. In another embodiment, the genome of the animal may contain an immunoglobulin light chain locus that encodes only a light chain constant region, i.e., a light chain that is not linked to a scaffold or variable domain. In these embodiments, the fusion protein encoded by the heavy chain locus and the light chain constant region encoded by the light chain locus, when expressed, link together via a disulfide bond. A resultant binding protein produced by this embodiment is illustrated in FIG. 2.

In a related embodiment, the animal may additionally comprise an immunoglobulin light chain locus comprising: a) a second transcribed gene encoding a second fusion protein comprising, from N-terminus to C-terminus: i. a second scaffold comprising a second binding domain; and ii. a light chain constant region operably linked to the scaffold; wherein the scaffold is capable of specifically binding to a target in the absence of additional polypeptides; and b) a plurality of pseudogenes that are operably linked to the second transcribed gene and that donate, by gene conversion, nucleotide sequence to the part of the second transcribed gene that encodes the second binding domain. In these embodiments, the first and second binding domains may have different binding specificities. A resultant binding protein produced by this embodiment is illustrated in FIG. 2. In particular cases, both the heavy and light chain immunoglobulin loci may be modified in a subject animal, and each arm of the resulting antibodies could have two independent binding sites. For example, the variable domain of an endogenous locus may be replaced with a scFv, and the pseudogene array would be comprised of an array of different scFvs. This could be done at both the heavy and light chain loci to achieve antibody-like molecules with dual specificities.

In some instances one may modify the distance between the scaffold and the constant region by using a linker sequence, and in some instances the scaffold may be so large that it is only possible to have one of them present on each arm of the antigen receptor. In this case, the light chain locus may be modified to express only a truncated VL that does not interfere with the bulky alternative scaffold that fused to the heavy chain C region.

In particular embodiments, part of the heavy chain locus, including the constant region, part of an intron region and the 3'UTR of the transcribed gene, may be endogenous to the animal and the remainder of the heavy chain locus, including the coding sequence of the transcribed gene, the remainder of the intron and the pseudogenes may be exogenous to the animal, i.e., made recombinantly and introduced into the animal proximal to the constant domain, part intron and 3' UTR in such a way that a transcribed gene is produced and the pseudogenes are capable of donating sequence to the transcribed gene by gene conversion. In certain cases the heavy chain locus of the animal may contain, in operable linkage: an intron region, a constant domain-encoding region and a 3' untranslated region, where the intron region, the constant domain-encoding region and the 3' untranslated region are endogenous to the genome of the transgenic animal, and a plurality of pseudogenes, where the plurality of pseudogenes are exogenous to the genome of the transgenic animal. Alternatively, the constant domain encoding region could also be exogenous to the genome of the transgenic animal.

Along similar lines, the part of the light chain locus that includes the constant domain-encoding region, part of an intron, and the 3'UTR of the transcribed gene may be endogenous to the animal and the remainder of the light chain locus, including the coding sequence of the transcribed gene, the remainder of the intron and the pseudogenes may be exogenous to the animal, i.e., made recombinantly and introduced into the animal proximal to the constant domain, part intron and 3' UTR in such a way that a transcribed gene is produced and the pseudogenes are capable of donating sequence to the transcribed gene by gene conversion. In certain cases the light chain locus of the animal may contain, in operable linkage: an intron region, a constant domain-encoding region and a 3' untranslated region; where the intron region, the constant domain-encoding region and the 3' untranslated region are endogenous to the genome of the transgenic animal and a plurality of pseudogenes, where the plurality of pseudogenes are exogenous to the genome of the transgenic animal.

A binding protein produced by a subject transgenic animal may contain an endogenous constant domain, allowing the binding protein to undergo class switching and affinity maturation, which allows the animal to undergo normal immune system development, and mount normal immune responses. In specific embodiments transgenic chickens have three endogenous constant regions in the heavy chain locus encoding IgM, IgY and IgA. During the early stages of B cell development, B cells express IgM. As affinity maturation proceeds, class switching converts the constant region into IgY or IgA. IgY provides humoral immunity to both adults and neonatal chicks which receive about 200 mg of IgY via a reserve deposited into egg yolk. IgA is found primarily in lymphoid tissues (eg. the spleen, Peyer's patches and Harderian glands) and in the oviduct.

With the exception of a relatively small number of amino acids arising as a result of mutations that occur independently of gene conversion during affinity maturation (which occur in, e.g., less than 10%, less than 5%, less than 3%, or less than 1% of the amino acids), the resultant scaffolds produced by the transgenic animal may be different to the initial scaffold by at least 1 amino acid, e.g., at least 5 amino acids, at least 10 amino acids, at least 20 amino acids, or more, up to about 50 amino acids. The resultant scaffold may bind to a target with at least 10×, e.g., at least 100×, at least 1000×, at least 10,000×, at least 100,000× or at least 1,000,000× or more affinity than then the initial scaffold.

The above-described transgenic animal may be made by replacing the endogenous variable regions in an endogenous immunoglobulin heavy chain locus of an animal with a plurality of pseudogenes constructed recombinantly. Methods for producing transgenic animals that use gene conversion to generate an antibody repertoire are known (see, e.g., Sayegh, Vet. Immunol. Immunopathol. 1999 72:31-7 and Kamihira, Adv. Biochem. Eng. Biotechnol. 2004 91: 171-89 for birds, and Bosze, Transgenic Res. 2003 12:541-53 and Fan, Pathol. Int. 1999 49: 583-94 for rabbits and Salamone J. Biotechnol. 2006 124: 469-72 for cow), as is the structure and/or sequence of the germline immunoglobulin heavy and light chain loci of many of those species (e.g., Butler Rev Sci Tech 1998 17:43-70 and Ratcliffe Dev Comp Immunol 2006 30: 101-118), the above-described animal may be made by routine methods given this disclosure. A strategy for making a subject animal is provided in FIG. 3.

A method of making a transgenic animal is provided. In certain embodiments, the method comprises: replacing the variable regions in the endogenous immunoglobulin heavy chain locus of the animal with a) region encoding a scaffold, as described above; and b) a plurality of pseudogenes. Upon integration of the construct, the scaffold region essentially becomes the transcribed variable region of the immunoglobulin locus of the transgenic animal, and the pseudogenes alter the sequence of the transcribed variable region by gene conversion. Gene conversion may result in the contribution of small (eg 1-10 nucleotides), moderate (10-30 nucleotides), or large (>30 nucleotides) segments of DNA from one or more of the donor pseudogenes to the transcribed scaffold. Gene conversion can transpire over many iterations, so multiple pseudogenes may contribute sequence to the transcribed gene. Since the process of gene conversion is highly variable in terms of which pseudogenes are selected, and the extent to which each is utilized in a given lymphocyte, a large and diverse antibody repertoire will result in the transgenic animal. Similar change may be made to the light chain locus, as described above.

As would be readily apparent, the method may include first deleting a region containing the variable regions in the endogenous immunoglobulin heavy chain locus of the animal (including the transcribed variable region and the pseudogene variable regions, and all sequences in between) to leave, e.g., a constant region sequence and part of the intron between the constant region sequence and the transcribed variable region; and then adding the transcribed gene, the remainder of the intron, and the plurality of pseudogenes to the locus of the mammal.

Figure 3A:
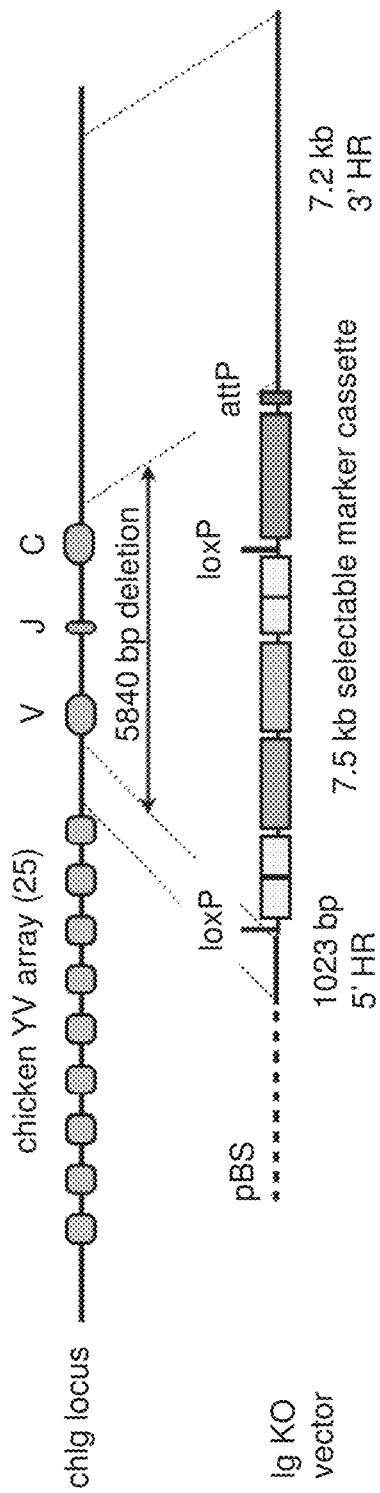
FIGS. 3A and 3B schematically illustrate a strategy for constructing an example of a subject immunoglobulin heavy chain locus.
Figure 3B:
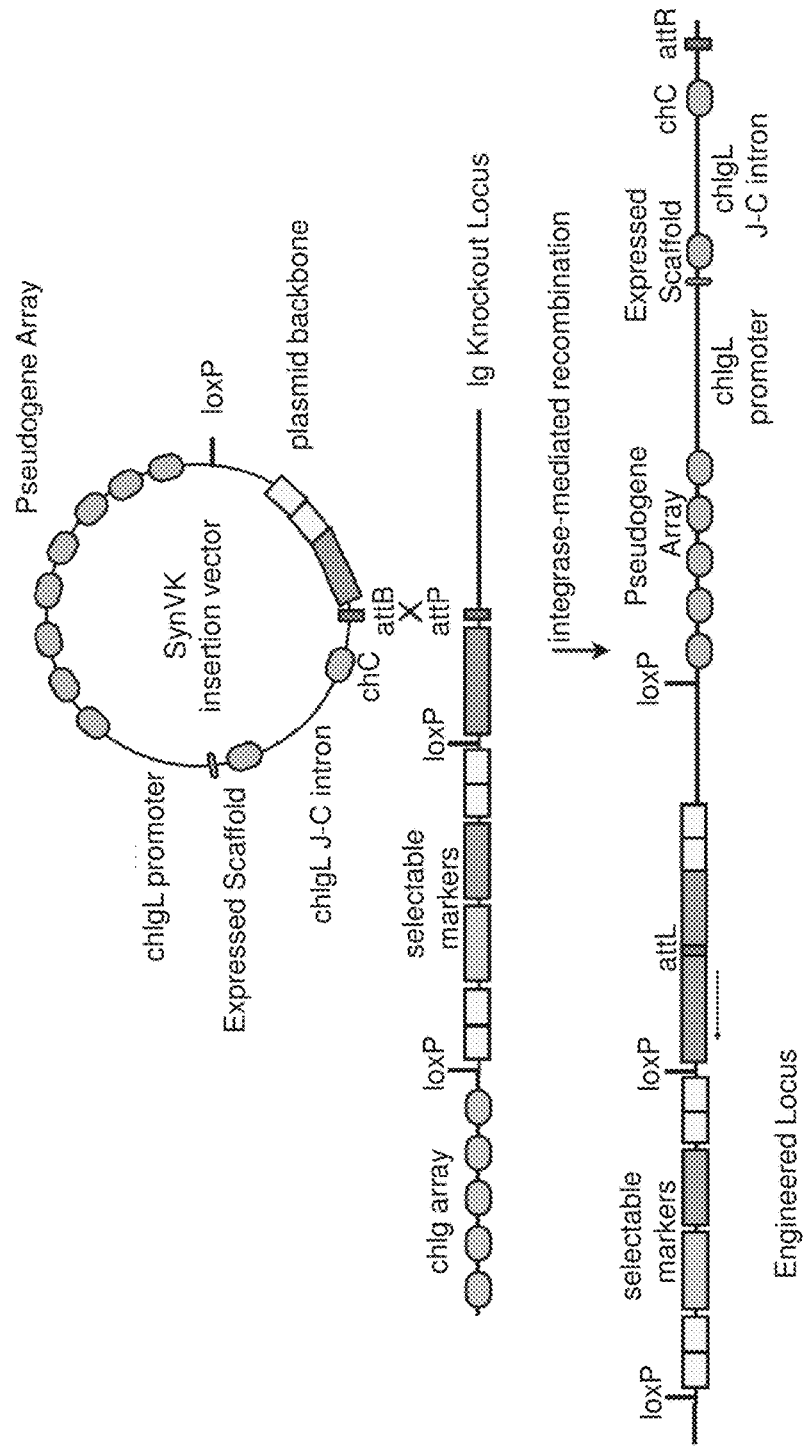

In particular embodiments and as schematically illustrated in FIG. 3, at least the variable region of the endogenous functional immunoglobulin gene of the transgenic animal may be replaced by a nucleic acid construct containing a plurality of pseudogene variable regions and a transcribed gene, without replacing the endogenous pseudogene variable regions of the transgenic animal. As such, the resultant immunoglobulin locus (which may be the heavy or light chain locus) may contain an array of endogenous pseudogenes in addition to an array of introduced pseudogenes upstream of a transcribed variable region.

Once made, the transgenic animal may be mated with other animals. In certain cases, the animal may be mated with siblings to produce an animal that is homozygous for the locus that produces no endogenous antibodies.

Once a subject transgenic animal is made, scaffolds that specifically bind to an antigen can be readily obtained by immunizing the animal with the antigen. A variety of antigens can be used to immunize a transgenic host animal. Such antigens include, microorganism, e.g. viruses and unicellular organisms (such as bacteria and fungi), alive, attenuated or dead, fragments of the microorganisms, or antigenic molecules isolated from the microorganisms. In certain embodiments, the animal may be immunized with: GD2, EGF-R, CEA, CD52, CD20, Lym-1, CD6, complement activating receptor (CAR), EGP40, VEGF, tumor-associated glycoprotein TAG-72 AFP (alpha-fetoprotein), BLyS (TNF and APOL—related ligand), CA125 (carcinoma antigen 125), CEA (carcinoembrionic antigen), CD2 (T-cell surface antigen), CD3 (heteromultimer associated with the TCR), CD4, CD11a (integrin alpha-L), CD14 (monocyte differentiation antigen), CD20, CD22 (B-cell receptor), CD23 (low affinity IgE receptor), CD25 (IL-2 receptor alpha chain), CD30 (cytokine receptor), CD33 (myeloid cell surface antigen), CD40 (tumor necrosis factor receptor), CD44v6 (mediates adhesion of leukocytes), CD52 (CAMPATH-1), CD80 (costimulator for CD28 and CTLA-4), complement component C5, CTLA, EGFR, eotaxin (cytokine A11), HER2/neu, HERS, HLA-DR, HLA-DR10, HLA ClassII, IgE, GPiib/iiia (integrin), Integrin aVβ3, Integrins a4β1 and a4β7, Integrin β2, IFN-gamma, IL-1β, IL-4, IL-5, IL-6R (IL6 receptor), IL-12, IL-15, KDR (VEGFR-2), lewisy, mesothelin, MUC1, MUC18, NCAM (neural cell adhesion molecule), oncofetal fibronectin, PDGFI3R (Beta platelet-derived growth factor receptor), PMSA, renal carcinoma antigen G250, RSV, E-Selectin, TGFbeta1, TGFbeta2, TNFα, DR4, DR5, DR6, VAP-1 (vascular adhesion protein 1) or VEGF, or the like in order to produce a therapeutic scaffold. In a particular cases, the animal may be immunized with an antigen to which the scaffold already binds.

The antigens can be administered to a transgenic host animal in any convenient manner, with or without an adjuvant, and can be administered in accordance with a predetermined schedule.

After immunization, serum or milk from the immunized transgenic animals can be fractionated for the purification of pharmaceutical grade binding proteins specific for the antigen. In the case of transgenic birds, antibodies can also be made by fractionating egg yolks. A concentrated, purified fraction may be obtained by chromatography (affinity, ionic exchange, gel filtration, etc.), selective precipitation with salts such as ammonium sulfate, organic solvents such as ethanol, or polymers such as polyethyleneglycol.

For making a monoclonal scaffold, antibody-producing cells, e.g., spleen cells, may be isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1, U.S. Pat. No. 4,977,081, WO 97/16537, and EP 0 491 057 B1, the disclosures of which are incorporated herein by reference. In vitro production of monoclonal antibodies from cloned cDNA molecules has been described by Andris-Widhopf et al., J Immunol Methods 242:159 (2000), and by Burton, Immunotechnology 1:87 (1995), the disclosures of which are incorporated herein by reference.

As such, in addition to the transgenic animal, a method comprising immunizing the transgenic animal with an antigen and obtaining from the transgenic animal a scaffold that specifically binds to the antigen is also provided. The method may include making hybridomas using cells of the transgenic animal; and screening the hybridomas to identify a hybridoma that produces a scaffold that specifically binds to the antigen.

Compositions comprising a fusion protein are also provided. In these embodiments, the fusion protein may comprise, from N-terminus to C-terminus: i. a scaffold comprising a first binding domain, as described above; and ii. a heavy chain constant region operably linked to the scaffold, as described above. As noted above, the scaffold is not from a classical antibody and the scaffold specifically binds to a selected target in the absence of additional polypeptides. The fusion protein may exist on its own, or complexed with one or more other proteins. In particular embodiments, the fusion protein may exist in a complex that may comprise a light chain protein that comprises a light chain constant region but not a light chain variable domain, wherein the light chain constant region and the heavy chain constant region of the fusion protein are linked by a disulfide bond. In additional embodiments, the fusion protein may exist in a complex that comprises a light chain protein that comprises: i. a scaffold comprising a second binding domain; and ii. a light chain constant region operably linked to the scaffold. In these embodiments, the scaffold is connected to the light chain constant region specifically binds to a selected target in the absence of additional polypeptides, and the light chain constant region and the heavy chain constant region are linked by a disulfide bond. As would be readily apparent, the binding specificities of the scaffold attached to the heavy chain constant region and the scaffold attached to the light chain constant region may be different and, as such, this protein may be bispecific in that it binds to two distinct molecular targets, or "biparatopic" (i.e. binding two distinct epitopes on the same molecular target).

Aspects of the present teachings can be further understood in light of the following example, which should not be construed as limiting the scope of the present teachings in any way.

Example

Figure 4:
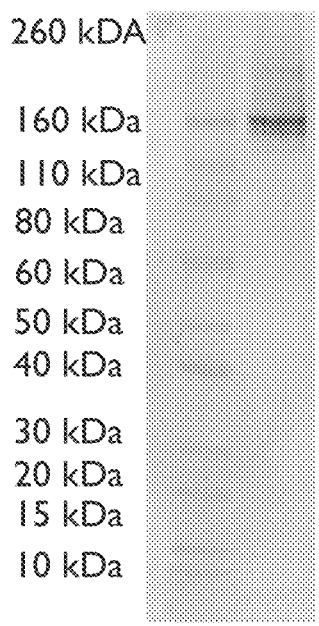
FIG. 4 shows an electroblot probed with anti-chicken IgY antibody

Alternative scaffold heavy chain and truncated light chain expression constructs (designed to produce a protein illustrated at the top of FIG. 2) were co-transfected into HEK 293 cells, and secreted product was recovered and run on SDS-PAGE under non-reducing conditions. The gel was electroblotted onto PVDF membrane and probed with anti-chicken IgY antibody. This heavy chain contained autonomous "camelized" human VH gene linked to the C regions of IgY. The light chain had a leader peptide linked directly to CL (100% truncation of VL). The expressed product migrated at the expected molecular weight (~160 kD) for dimeric heavy chain paired with light chain. The results (shown in FIG. 4) confirm that truncated light chain can support the proper processing and secretion of novel scaffolds when they are genetically fused to the appropriate heavy chain constant regions.

What is claimed is:

1. An isolated antibody-producing cell of a transgenic chicken that uses gene conversion for developing its primary antibody repertoire, wherein the antibody-producing cell secretes a fusion protein that specifically binds to an antigen, and wherein the transgenic chicken comprises a genome comprising an immunoglobulin heavy chain locus comprising:
   a) a transcribed gene encoding a fusion protein comprising, from N-terminus to C-terminus:
      i. a scaffold comprising a first binding domain; and operably linked to said scaffold: ii. a heavy chain constant region that is native to said chicken;
      wherein said scaffold is capable of specifically binding to a target in the absence of additional polypeptides; and
   b) a plurality of pseudogenes that are operably linked to said transcribed gene and that donate, by gene conversion, nucleotide sequence to the part of said transcribed gene that encodes said binding domain, wherein the pseudogenes are upstream or downstream of the transcribed gene and contain a nucleotide sequence that is at least 80% identical to at least part of the transcribed gene.

2. The isolated antibody-producing cell of claim 1, wherein the genome of the transgenic chicken comprises an immunoglobulin light chain locus that encodes a light chain constant region but not a light chain variable domain.

3. The isolated antibody-producing cell of claim 1, wherein the genome of the transgenic chicken comprises an immunoglobulin light chain locus comprising:
   a) a second transcribed gene encoding a second fusion protein comprising, from N-terminus to C-terminus:
      i. a second scaffold comprising a second binding domain; and
      ii. a light chain constant region operably linked to said scaffold;
      wherein said scaffold is capable of specifically binding to a target in the absence of additional polypeptides; and
   b) a plurality of pseudogenes that are operably linked to said second transcribed gene and that donate, by gene conversion, nucleotide sequence to the part of said second transcribed gene that encodes said second binding domain, wherein the pseudogenes lined to the second transcribed gene are upstream or downstream of the second transcribed gene and contain a nucleotide sequence that is at least 80% identical to at least part of the second transcribed gene.

4. The isolated antibody-producing cell of claim 3, wherein said first and second binding domains have different binding specificities.

5. The isolated antibody-producing cell of claim 1, wherein said scaffold is single-chain antibody.

6. The isolated antibody-producing cell of claim 5, wherein said single-chain antibody comprises heavy and light chains from a classical antibody that are linked in a single polypeptide chain.

7. The isolated antibody-producing cell of claim 5, wherein said single-chain antibody is a VHH (variable heavy-heavy) antibody.

8. The isolated antibody-producing cell of claim 7, wherein said single-chain antibody is a humanized VHH antibody.

9. The isolated antibody-producing cell of claim 1, wherein said scaffold is not antibody derived.

10. The isolated antibody-producing cell of claim 1, wherein the nucleotide sequences of said pseudogenes are at least 80% identical to the nucleotide sequence of said part of said transcribed gene.

11. The isolated antibody-producing cell of claim 1, wherein said immunoglobulin heavy chain locus comprises at least 10 of said pseudogenes.

12. The isolated antibody-producing cell of claim 1, wherein said transgenic chicken is made by replacing the endogenous variable region in an endogenous immunoglobulin heavy chain locus of the transgenic chicken with a nucleic acid construct comprising said plurality of pseudogenes and encoding said scaffold, without replacing the constant region of said endogenous immunoglobulin heavy chain locus.

13. The isolated antibody-producing cell of claim 1, wherein at least one of said plurality of pseudogenes is in reverse orientation relative to said transcribed gene.

14. The isolated antibody-producing cell of claim 1, wherein said cell is a B cell.

15. A hybridoma made by fusing an isolated antibody-producing cell of claim 1 and another cell.

* * * * *